United States Patent [19]

Bäckström et al.

[11] Patent Number: 6,004,574

[45] Date of Patent: Dec. 21, 1999

[54] POWDER FORMULATIONS CONTAINING MELEZITOSE AS A DILUENT

[75] Inventors: Kjell Bäckström; Ann Johansson; Helena Lindén, all of Lund, Sweden

[73] Assignee: Astra Aktiebolag, Sweden

[21] Appl. No.: 08/617,753

[22] PCT Filed: Dec. 19, 1995

[86] PCT No.: PCT/SE95/01541

§ 371 Date: Mar. 18, 1996

§ 102(e) Date: Mar. 18, 1996

[87] PCT Pub. No.: WO96/19207

PCT Pub. Date: Jun. 27, 1996

[30] Foreign Application Priority Data

Dec. 22, 1994 [SE] Sweden .................................. 9404468

[51] Int. Cl.⁶ .............................. A61K 9/14; A61K 9/127
[52] U.S. Cl. ..................... 424/434; 424/489; 424/470; 424/461; 424/450; 424/45
[58] Field of Search ...................... 424/489, 464, 424/465, 404.45, 450, 400

[56] References Cited

U.S. PATENT DOCUMENTS

| | | |
|---|---|---|
| 3,014,844 | 12/1961 | Thiel et al. . |
| 3,671,625 | 6/1972 | Altounyan . |
| 4,232,002 | 11/1980 | Nogrady . |
| 4,462,983 | 7/1984 | Azria . |
| 4,613,500 | 9/1986 | Suzuki et al. . |
| 4,690,952 | 9/1987 | Kagatani et al. . |
| 4,788,221 | 11/1988 | Kagatani et al. . |
| 4,895,719 | 1/1990 | Radhakrishnan et al. . |
| 5,011,678 | 4/1991 | Wang et al. . |
| 5,179,079 | 1/1993 | Hansen et al. . |
| 5,202,129 | 4/1993 | Samejima et al. . |
| 5,284,656 | 2/1994 | Platz et al. . |
| 5,341,800 | 8/1994 | Clark et al. . |
| 5,354,562 | 10/1994 | Platz et al. . |
| 5,506,203 | 4/1996 | Bäckström et al. . |
| 5,518,998 | 5/1996 | Bäckström et al. . |

FOREIGN PATENT DOCUMENTS

| | | |
|---|---|---|
| 0 023 359 | 7/1980 | European Pat. Off. . |
| 0 133 252 A2 | 2/1985 | European Pat. Off. . |
| 0 272 097 A2 | 6/1988 | European Pat. Off. . |
| 0 364 235 | 11/1989 | European Pat. Off. . |
| 0 360 340 A1 | 3/1990 | European Pat. Off. . |
| 0 364 235 A1 | 4/1990 | European Pat. Off. . |
| 9302198-8 | 6/1993 | Sweden . |
| 9400371-2 | 2/1994 | Sweden . |
| 87/05213 | 9/1987 | WIPO . |
| 87/05213 A1 | 9/1987 | WIPO . |
| 91/16038 A1 | 10/1991 | WIPO . |
| 91/18091 A1 | 11/1991 | WIPO . |
| 94/07514 A1 | 4/1994 | WIPO . |

OTHER PUBLICATIONS

Björk, Degradable Startch Microspheres as a Nasal Delivery System for Insulin, ACTA Univ. Appsala, Comprehensive Summaries of Uppsala Dissertations from the Faculty of Pharmacy 103, 1993.

Björk, Starch Microspheres as a Nasal Delivery System for Drugs, ACTA Univ. Upsaliensis, Uppsala, Comprehensive Summaries of Uppsala Dissertations from the FAculty of Pharmacy, 103: parts 1–5, 1993.

Komada et al., Intratracheal Delivery of Peptide and Protein Agents: Absorption from Solution and Dry Powder by Rat Lung, J. Pharm. Sci. 83:863–867, 1994.

Lee et al., Internasal Bioavailability of Insulin Powder Formulations: Effect of Permeation Enhancer–to–Protein Ratio, J. Pharm. Sci. 80:725–729, 1991.

Nagai et al., Powder Dosage Form of Insulin for Nasal Administration, J. Controlled Release 1:15–22, 1984.

Schipper et al., Nasal Insulin Delivery with Dimethyl–β–Cyclodextrin as an Absorption Enhancer in Rabbits: Power more Effective than Liquid Formulations, Pharmaceutical Research 10:682–686, 1993.

Trimsina et al., Drug Delivery to the Respiratory Tract Using Dry Powder Inhalers, Int. J. Pharmaceutics 101:1–13, 1994.

Wearley, Recent Progress in Protein and Peptide Delivery by Noninvasive Routes, Critical Reviews in Therapeutic Drug Carrier Systems, 8(4):331–94, 1991.

*Primary Examiner*—Thurman K. Page
*Assistant Examiner*—William E. Benston, Jr.
*Attorney, Agent, or Firm*—Fish & Richardson P.C.

[57] ABSTRACT

A powder formulation for the administration of medically useful polypeptides, comprising a medically useful polypeptide with melezitose as diluent.

72 Claims, No Drawings

POWDER FORMULATIONS CONTAINING MELEZITOSE AS A DILUENT

This application is a 371 of PCT/SE95/01541 filed Dec. 19, 1995.

FIELD OF THE INVENTION

The present invention relates to powder formulations containing medically useful polypeptides.

TECHNICAL BACKGROUND

Polypeptide powders containing medically useful polypeptides and pharmaceutically acceptable carriers or diluents may be prepared for administration by inhalation or otherwise. Inhalable polypeptide powder preparations have been described in WO95/00127 and WO95/00128.

Diluents are commonplace in pharmaceutical preparations, especially in formulations for inhalation. They are used to stabilise various drugs during manufacture and storage and to adjust the amount of powder making up unit doses—in general, powder inhalers are capable of delivering a drug substance with good dose accuracy only for certain dose sizes, while different drugs have different potencies and must therefore be delivered in different amounts. As these amounts are often too small for proper dose accuracy to be ensured, diluents are added to give the desired dose size.

Previously, reducing sugars such as lactose and glucose have been used as diluents in polypeptide powder formulations. These however have a tendency to react with polypeptides and are therefore unsatisfactory.

It is suggested in WO95/00127 and WO95/00128, relating to polypeptide powders for inhalation, that non-reducing sugars such as raffinose, melezitose, lactitol, maltitol, trehalose, sucrose, mannitol and starch may be preferred additives for the polypeptide powders.

It has now been found that melezitose is an exceptionally good diluent compared with other possible non-reducing sugar diluents for polypeptide powder formulations, giving an unexpectedly high respirable fraction of powder when inhaled.

SUMMARY OF THE INVENTION

Accordingly, the present invention provides a powder formulation for the administration of medically useful polypeptides, comprising a medically useful polypeptide with melezitose as diluent.

Administration is preferably by inhalation.

The melezitose may comprise for example D-melezitose (α-D-melezitose), 0-α-D-glucopyranosyl-1,3,-β-D-fructofuranosyl-β-D-glucopyranoside(β-D-melezitose) or isomelezitose. The melezitose may be for example in the form of the monohydrate or dihydrate.

The powder formulation of the present invention has been found to be very effective upon oral inhalation, giving a superior fraction of respirable particles compared with powder formulations with other diluents, as is described herein. As a result, a higher fraction of the inhaled powder will reach the lungs and a higher fraction of the polypeptide is utilised.

The powder formulation of the present invention is also suitable for use in nasal inhalation.

The powder formulation of the present invention is suitable for both systemic and local treatment. When local action is desired in the respiratory tract, no other ingredient is necessary in the powder formulation. When systemic action is required, an enhancer, i.e. a substance which enhances the absorption of the polypeptide in the respiratory tract, should generally be included in the formulation. Such substances are included in WO95/00127 and WO95/00128, incorporated herein by reference. In certain cases, small polypeptides are absorbed in the respiratory tract without the aid of an enhancer. In these cases an enhancer may be excluded from the formulations of melezitose and the medically useful polypeptide. In different embodiments therefore the present invention provides a powder comprising a medically useful polypeptide and melezitose; a powder comprising a medically useful polypeptide and melezitose and specifically including an enhancer; and a powder comprising a medically useful polypeptide and melezitose, specifically excluding an enhancer. The powder according to the present invention excluding an enhancer, is most useful (a) when local action of the polypeptide is desired; or (b) when systemic action of smaller polypeptides which are absorbed in the respiratory tract without the aid of an enhancer is desired. Polypeptides which are absorbed in the respiratory tract without the aid of an enhancer may be identified using conventional cell or, preferably, animal models, in the latter case by comparing plasma polypeptide levels following administration, for example by means of a Wright Dust Feed apparatus, of powders with and without enhancer. The powder specifically including an enhancer according to the present invention, is most useful when systemic action of polypeptides which are not absorbed in the respiratory tract without the aid of an enhancer, is desired.

Preferred enhancers include $C_{8-16}$ fatty acids and salts thereof, bile salts, phospholipids and alkyl saccharides.

Of the fatty acids and salts thereof, $C_8$–$C_{16}$ fatty acids salts are preferred. Examples of preferred fatty acid salts are sodium, potassium and lysine salts of caprylate ($C_8$), caprate ($C_{10}$), laurate ($C_{12}$) and myristate ($C_{14}$). As the nature of the counterion is not of special significance, any of the salts of the fatty acids are potentially useful. A particularly preferred fatty acid salt is sodium caprate.

Suitable bile salts may be for example salts of cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid.

Of the bile salts, trihydroxy bile salts are preferred. More preferred are the salts of cholic, glycocholic and taurocholic acids, especially the sodium and potassium salts thereof. The most preferred bile salt is sodium taurocholate.

Suitable phospholipids may be for example single-chain phospholipids, for example lysophosphatidylcholines, lysophosphatidylglycerols, lysophosphatidylethanolamines, lysophosphatidylinositols and lysophosphatidylserines or double-chain phospholipids, for example diacylphosphatidylcholines, diacylphosphatidylglycerols, diacylphosphatidylethanolamines, diacylphosphatidylinositols and diacylphosphatidylserines.

Of the phospholipids, diacylphosphatidylglycerols and diacylphosphatidylcholines are preferred, for example dioctanoylphosphatidylglycerol and dioctanoylphosphatidylcholine.

Suitable alkyl saccharides may be for example alkyl glucosides or alkyl maltosides, such as decyl glucoside and dodecyl maltoside.

The most preferred enhancers are bile salts.

The polypeptide may be any medically or diagnostically useful peptide or protein of small to medium size, i.e. up to about 40 kD molecular weight (MW). It is expected that polypeptides having a molecular weight of up to 30 kD will be most useful in the present invention, such as polypeptides having a molecular weight of up to 25 kD or up to 20 kD, and especially up to 15 kD, up to 10 kD, or up to 5 kD.

The polypeptide is preferably a peptide hormone such as insulin, glucagon, C-peptide of insulin, vasopressin, desmopressin, corticotropin (ACTH), corticotropin releasing hormone (CRH), gonadotropin releasing hormone (GnRH), gonadotropin releasing hormone agonists and antagonists, gonadotrophin (luteinizing hormone, or LHRH), calcitonin, parathyroid hormone (PTH), bioactive fragments of PTH such as PTH(34) and PTH(38), growth hormone (GH) (for example human growth hormone (hGH)), growth hormone releasing hormone (GHRH), somatostatin, oxytocin, atrial natriuretic factor (ANF), thyrotropin releasing hormone (TRH), deoxyribonuclease (DNase), prolactin, and follicle stimulating hormone (FSH), and analogues of any of the above.

Other possible polypeptides include growth factors, interleukins, polypeptide vaccines, enzymes, endorphins, glycoproteins, lipoproteins, and polypeptides involved in the blood coagulation cascade.

The preferred polypeptide is insulin.

In the powder formulation of the present invention melezitose may be present in an amount of up to almost 100% by weight of the total powder. For example the melezitose may be present in an amount between 20% and almost 100%, for example between 30% and almost 100% or between 40% and almost 100%, or between 50% and almost 100%, e.g between 60% and almost 100%, between 65% and almost 100%, such as between 65% and 99% or between around 70% and around 99% such as between 80% and 98% by weight of the total weight of powder.

As with all pharmaceutical preparations, certain additives, for example for pH regulation, for example organic or inorganic salts, to give taste, or to increase stability, for example preservatives, carbohydrates, amino acids, peptides and proteins, may also be included in the formulation.

When the powder preparation of the present invention is intended for oral inhalation the polypeptide should consist of (a) primary particles having a diameter of less than about 10 microns, for example between 0.01 and 10 microns and preferably between 0.1 and 6 microns, for example between 0.01 and 5 micons, or (b) agglomerates of said particles. Preferably at least 50% of the polypeptide consists of particles within the desired size range. For example at least 60%, preferably at least 70%, more preferably at least 80% and most preferably at least 90% of the polypeptide consists of particles within the desired size range, when oral inhalation is desired.

The melezitose in the formulation for oral inhalation may largely consist of particles having a diameter of less than about 10 microns so that the resultant powder as a whole consists of optionally agglomerated primary particles having a diameter of less than about 10 microns; alternatively the melezitose may largely consist of much bigger particles ("coarse particles"), so that an "ordered mixture" may be formed between the active compounds and the melezitose. In the ordered mixture, alternatively known as an interactive or adhesive mixture, the polypeptide particles will be fairly evenly distributed over the surface of the coarse melezitose. Preferably in such case the active compounds are not in the form of agglomerates prior to formation of the ordered mixture. The coarse particles may have a diameter of over 20 microns, such as over 60 microns. Above these lower limits, the diameter of the coarse particles is not of critical importance so various coarse particle sizes may be used, if desired according to the practical requirements of the particular formulation. There is no requirement for the coarse particles in the ordered mixture to be of the same size, but the coarse particles may advantageously be of similar size within the ordered mixture. Preferably, the coarse particles have a diameter of 60–800 microns.

The particle size is less important in nasal inhalation although small particles are desirable. An ordered mixture would not normally be employed in nasal inhalation.

A useful mechanism for delivery of the powder into the respiratory tract of a patient is through a portable inhaler device suitable for dry powder inhalation. Many such devices, typically designed to deliver antiasthmatic or anti-inflammatory agents into the respiratory system, are on the market.

The described powder preparation can be manufactured in several ways, using conventional techniques. Particles in a required size range may be obtained by any known method, for example by freeze-drying or by controlled crystallisation methods, for example crystallisation using supercritical fluids; or by micronisation methods. For example, one can dry mix the polypeptide and melezitose (and optional enhancer) powders, and then micronise the substances together; alternatively, the substances can be micronised separately, and then mixed. Where the compounds to be mixed have different physical properties such as hardness and brittleness, resistance to micronisation varies and they may require different pressures to be broken down to suitable particle sizes. When micronised together, therefore, the obtained particle size of one of the components may be unsatisfactory. In such case it would be advantageous to micronise the different components separately and then mix them.

It is also possible, where an ordered mixture is not intended, first to dissolve the components in a suitable solvent, e.g. water, to obtain mixing on the molecular level. This procedure also makes it possible to adjust the pH-value to a desired level. To obtain a powder, the solvent must be removed by a process which retains the polypeptide's biological activity. Suitable drying methods include vacuum concentration, open drying, spray drying, and freeze drying. Temperatures over 40° C. for more than a few minutes should generally be avoided, as some degradation of the polypeptide may occur. Following the drying step, the solid material can, if necessary, be ground to obtain a coarse powder, then, if necessary, micronised.

If desired, the powder can be processed to improve the flow properties, e.g., by dry granulation to form spherical agglomerates with superior handling characteristics, before it is incorporated into the intended inhaler device. In such a case, the device would be configured to ensure that the agglomerates are substantially deagglomerated prior to exiting the device, so that the particles entering the respiratory tract of the patient are largely within the desired size range.

Where an ordered mixture is desired, the active compound may be processed, for example by micronisation, in order to obtain, if desired, particles within a particular size range. The melezitose may also be processed, for example to obtain a desired size and desirable surface properties, such as a particular surface to weight ratio, or a certain ruggedness, and to ensure optimal adhesion forces in the ordered mixture. Such physical requirements of an ordered mixture are well known, as are the various means of obtaining an ordered mixture which fulfills the said requirements, and may be determined easily by the skilled person according to the particular circumstances.

The powders of the present invention are useful for the local or systemic treatment of diseases and may be administered for example via the upper and lower respiratory tract, including by the nasal route. As such the present invention also provides said powder for use in therapy; the use of the powder in the manufacture of a medicament for the treatment of diseases via the respiratory tract; and a method for the treatment of a patient in need of therapy, comprising administering to said patient a therapeutically effective amount of the powder of the present invention.

The diseases which may be treated with the powder of the present invention are any of those which may be treated with the particular polypeptide in each case; for example powders containing insulin according to the present invention may be used for example in the treatment of diabetes; powders containing corticotropin may be used for example in the treatment of inflammatory diseases; powders containing GnRH may be useful for example in the treatment of male infertility. The indications for all of the mentioned polypeptides are well known. The powders of the present invention may also be used in prophylactic treatment.

Although the powders of the present invention are particularly directed to polypeptide powders for inhalation from dry powder inhaler devices, the polypeptide powders may also be included in compositions for other forms of administration, for example in injection solutions and aerosol formulations.

The respirable fraction upon oral inhalation of the powders of the present invention may be determined by the method described in the Examples herein.

Certain embodiments of the invention are illustrated in the following Examples, which are not to be considered limiting:

EXAMPLE 1

Insulin (0.6 g) was dissolved in distilled water (50 ml). Diluent (14.4 g) was added and dissolved and the pH was adjusted to 7.4. The obtained solid cake was crushed, sieved, and micronised in a jet mill. The micronised powders were agglomerated and filled into a Turbuhaler® dry powder inhaler and the dose was released at an air flow rate of 60 L/min, under varying conditions.

The released dose was collected using a multi-stage impinger; the content of insulin in each stage of the impinger was determined using liquid chromatography with detection at 235 nm. The results were as follows.

| fraction of particles of size less than 6.8 µm, % Diluent | 30% RH, 60 L/min | 75% RH, 60 L/min | 30% RH, 60 L/min, open moisture provocation** |
|---|---|---|---|
| myo-inositol | 52 | 18 | 3 |
| maltitol | 66 | 10 | 8 |
| mannitol | 65 | 17 | 9 |
| trehalose | 58 | 22 | 17 |
| raffinose | 40 | 17 | |
| palatinite | 30 | 18 | 15 |
| stachyose | 52 | 5 | |
| melezitose | 73 | 39 | 32 |

**the preparation had been moisture provocated for three days in open plates.

the preparation had been moisture provocated for three days in open plates.

It is clearly seen that melezitose gave the highest fraction of respirable particles in all cases. Moreover the respirable fraction is not as dependent on external factors when melezitose is the diluent.

EXAMPLE 2

Insulin (12 parts) was dissolved in distilled water. Sodium taurocholate (enhancer, 4 parts) was added. Various diluents (84 parts) were added and dissolved and the pH was adjusted to 7.4. The solution was concentrated by evaporation of the water. The obtained solid cake was crushed, sieved, and micronised in a jet mill. The micronised powder was agglomerated and filled into a Turbuhaler® dry powder inhaler and the dose was released at an air flow rate of 60 L/min, under varying conditions.

The released dose was collected using a multi-stage impinger; the content of insulin in each stage of the impinger was determined using liquid chromatography with detection at 235 nm. The results were as follows.

| Fraction of particles of size less than 6.8 μm, % | 30% RH 60 L/min | 90% RH 60 L/min |
|---|---|---|
| melezitose | 65.0 | 21.7 |
| trehalose | 60.5 | 6.3 |
| myo-inositol | 71.6 | 10.9 |
| mannitol | 79.4 | 4.4 |
| maltitol | 44.7 | 0.1 |

These results show that the formulation with melezitose is much less affected by high humidity in the air.

EXAMPLE 3

Micronised formulations containing DNase, surfactant (sodium taurocholate or dioctanoylphosphatidylglcerol), and melezitose (ratio DNase: surfactant: melezitose 1:0.33:98.67, total weight 50 mg), were added to propellant 134a or propellant 227 (approximately 10 ml) in a plastic coated glass bottle. The formulations were mixed with an ultra turrax for approximately 10 minutes.

Identical formulations were prepared to which 5% of ethanol was added prior to the mixing with an ultraturrax apparatus for approximately 10 minutes.

The quality of the suspensions formed were assessed immediately and after 20 hours. In all cases good suspensions were observed.

This shows that the melezitose-containing formulations of the present invention are suitable for use in formulations other than for dry-powder inhalation, in this case in aerosol formulations.

It is claimed:

1. A powder formulation for the administration of a medically useful polypeptide by inhalation, consisting of a powder comprising a medically useful polypeptide with melezitose as diluent.

2. A powder formulation as claimed in claim 1, wherein the melezitose comprises D-melezitose (α-D-melezitose); 0-α-D-glucopyranosyl-1,3-β-D-fructofuranosyl-β-D-glucopyranoside (β-D-melezitose); or isomelezitose.

3. A powder formulation as claimed in claim 1, wherein the melezitose is in the form of a monohydrate or dihydrate.

4. A powder formulation as claimed in claim 1, wherein the powder includes an enhancer which enhances the absorption of the medically useful polypeptide in the lower respiratory tract.

5. A powder formulation as claimed in claim 4, wherein the enhancer is selected from the group consisting of $C_{8-16}$ fatty acids and salts thereof, bile salts, phospholipids and alkyl saccharides.

6. A powder formulation as claimed in claim 4, wherein the enhancer is selected from the sodium, potassium and lysine salts of caprylate ($C_8$), caprate ($C_{10}$), laurate ($C_{12}$) and myristate ($C_{14}$).

7. A powder formulation as claimed in claim 4, wherein the enhancer is a bile salt selected from the group consisting of salts of cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid.

8. A powder formulation as claimed in claim 4, wherein the enhancer is a trihydroxy bile salt.

9. A powder formulation as claimed in claim 4, wherein the enhancer is selected from the group consisting of salts of cholic, glycocholic and taurocholic acids.

10. A powder formulation as claimed in claim 4, wherein the enhancer is selected from the group consisting of sodium and potassium salts of cholic, glycocholic and taurocholic acids.

11. A powder formulation as claimed in claim 4, wherein the enhancer is sodium taurocholate.

12. A powder formulation as claimed in claim 4, wherein the enhancer is a single-chain phospholipid.

13. A powder formulation as claimed in claim 4, wherein the enhancer is selected from the group consisting of lysophosphatidylcholines, lysophosphatidylglycerols, lysophosphatidylethanolamines, lysophosphatidylinositols and lysophosphatidylserines.

14. A powder formulation as claimed in claim 4, wherein the enhancer is a double-chain phospholipid.

15. A powder formulation as claimed in claim 4, wherein the enhancer is selected from the group consisting of diacylphosphatidylcholines, diacylphosphatidylglycerols, diacylphosphatidylethanolamines, diacylphosphatidylinositols and diacylphosphatidylserines.

16. A powder formulation as claimed in claim 4, wherein the enhancer is selected from the group consisting of dioctanoylphosphatidylglycerol, and dioctanoylphosphatidylcholine.

17. A powder formulation as claimed in claim 4, wherein the enhancer is selected from the group consisting of alkyl glucosides and alkyl maltosides.

18. A powder formulation as claimed in claim 1, wherein the polypeptide is selected from insulin, glucagon, C-peptide of insulin, vasopressin, desmopressin, corticotropin (ACTH), corticotropin releasing hormone (CRH), gonadotropin releasing hormone (GnRH), gonadotropin releasing hormone agonists and antagonists, gonadotrophin (luteinizing hormone, or LHRH), calcitonin, parathyroid hormone (PTH), bioactive fragments of PTH, growth hormone (GH), growth hormone releasing hormone (GHRH), somatostatin, oxytocin, atrial natriuretic factor (ANF), thyrotropin releasing hormone (TRH), deoxyribonuclease (DNase), prolactin, follicle stimulating hormone (FSH), and analogues thereof.

19. A powder formulation as claimed in claim 1, wherein the polypeptide is of molecular weight (MW) up to about 40 kD.

20. A powder formulation as claimed in claim 19, wherein the polypeptide has a molecular weight of up to 30 kD.

21. A powder formulation as claimed in claim 19, wherein the polypeptide has a molecular weight of up to 25 kD.

22. A powder formulation as claimed in claim 19, wherein the polypeptide has a molecular weight of up to 20 kD.

23. A powder formulation as claimed in claim 19, wherein the polypeptide has a molecular weight of up to 15 kD.

24. A powder formulation as claimed in claim 19, wherein the polypeptide has a molecular weight of up to 10 kD.

25. A powder formulation as claimed in claim 19, wherein the polypeptide has a molecular weight of up to 5 kD.

26. A powder formulation as claimed in claim 1, wherein the polypeptide is insulin.

27. A powder formulation as claimed in claim 1, wherein the melezitose is present in an amount of between 20% and almost 100% by weight of the powder.

28. A powder formulation as claimed in claim 27, wherein the melezitose is present in an amount of between 30% and almost 100% by weight of the powder.

29. A powder formulation as claimed in claim 28, wherein the melezitose is present in an amount of between 40% and almost 100% by weight of the powder.

30. A powder formulation as claimed in claim 29, wherein the melezitose is present in an amount of between 50% and almost 100% by weight of the powder.

31. A powder formulation as claimed in claim 30, wherein the melezitose is present in an amount of between 60% and almost 100% by weight of the powder.

32. A powder formulation as claimed in claim 31, wherein the melezitose is present in an amount of between 65% and almost 100% by weight of the powder.

33. A powder formulation as claimed in claim 32, wherein the melezitose is present in an amount of between 65% and 99% by weight of the powder.

34. A powder formulation as claimed in claim 33, wherein the melezitose is present in an amount of between 70% and 99% by weight of the powder.

35. A powder formulation as claimed in claim 34, wherein the melezitose is present in an amount of between 80% and 98% by weight of the powder.

36. A powder formulation as claimed in claim 1, wherein at least 50% of the polypeptide in the formulation consists of (a) primary particles having a diameter of between 0.01 and 10 microns, or (b) agglomerates of said particles.

37. A powder formulation as claimed in claim 1, wherein at least 50% of the polypeptide in the formulation consists of (a) primary particles having a diameter of between 1 and 6 microns, or (b) agglomerates of said particles.

38. A powder formulation as claimed in claim 36, wherein at least 60% of the polypeptide in the formulation consists of (a) primary particles having a diameter of between 0.01 and 10 microns, or (b) agglomerates of said particles.

39. A powder formulation as claimed in claim 38, wherein at least 70% of the polypeptide in the formulation consists of (a) primary particles having a diameter of between 0.01 and 10 microns, or (b) agglomerates of said particles.

40. A powder formulation as claimed in claim 39, wherein at least 80% of the polypeptide in the formulation consists of (a) primary particles having a diameter of between 0.01 and 10 microns, or (b) agglomerates of said particles.

41. A powder formulation as claimed in claim 40, wherein at least 90% of the polypeptide in the formulation consists of (a) primary particles having a diameter of between 0.01 and 10 microns, or (b) agglomerates of said particles.

42. A powder formulation as claimed in claim 1, wherein the melezitose consists essentially of particles having a diameter of less than about 10 microns.

43. A powder formulation as claimed in claim 1, wherein the melezitose consists essentially of particles of diameter over 20 microns.

44. A powder formulation as claimed in claim 43, wherein the melezitose consists essentially of particles having a diameter of 60–800 microns.

45. A powder formulation as claimed in claim 1, wherein no enhancer is included in the powder.

46. A method for the manufacture of a powder formulation as claimed in claim 1, comprising the steps of drying mixing the polypeptide and melezitose, and micronising the substances together.

47. A method for the manufacture of a powder formulation as claimed in claim 1, comprising the steps of micronising the polypeptide to produce a micronised polypeptide powder; separately micronising the melezitose to produce a micronised melezitose powder; and mixing the micronised powders.

48. A method for the manufacture of a powder formulation as claimed in claim 1, comprising the steps of dissolving the components in a solvent to produce a solution: and removing the solvent from the solution to produce a solid.

49. A method for the manufacture of a powder formulation as claimed in claim 43, comprising dry mixing the melezitose and a micronised polypeptide powder.

50. A method for the treatment of a patient in need of therapy, comprising administering to said patient a therapeutically effective amount of a powder formulation as claimed in claim 1.

51. The method of claim 50, wherein the medically useful polypeptide is insulin.

52. The method of claim 50, wherein the powder formulation is administered by providing it to the patient for inhalation.

53. The method of claim 50, wherein the powder formulation is administered from a dry powder inhaler device.

54. The method of claim 50, wherein the powder formulation is provided suspended in a propellant, and is administered from an aerosol inhaler device.

55. The method of claim 50, wherein the powder includes an enhancer which enhances the absorption of the medically useful polypeptide in the lower respiratory tract.

56. The method of claim 55, wherein the enhancer is selected from the group consisting of $C_{8-16}$ fatty acids and salts thereof, bile salts, phospholipids and alkyl saccharides.

57. The method of claim 55, wherein the enhancer is selected from the sodium, potassium and lysine salts of caprylate ($C_8$), caprate ($C_{10}$), laurate ($C_{12}$), and myristate ($C_{14}$).

58. The method of claim 55, wherein the enhancer is a bile salt selected from the group consisting of salts of cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid.

59. The method of claim 55, wherein the enhancer is selected from the group consisting of sodium and potassium salts of cholic, glycocholic and taurocholic acids.

60. The method of claim 55, wherein the enhancer is sodium taurocholate.

61. The method of claim 55, wherein the enhancer is a single-chain phospholipid.

62. The method of claim 55, wherein the enhancer is a double-chain phospholipid.

63. The method of claim 55, wherein the enhancer is selected from the group consisting of alkyl glucosides and alkyl maltosides.

64. The method of claim 50, wherein the polypeptide is selected from the group consisting of insulin, glucagon, C-peptide of insulin, vasopressin, desmopressin, corticotropin (ACTH), corticotropin releasing hormone (CRH), gonadotropin releasing hormone (GnRH), gonadotropin releasing hormone agonists and antagonists, gonadotrophin (luteinizing hormone, or LHRH), calcitonin, parathyroid hormone (PTH), bioactive fragments of PTH, growth hormone (GH), growth hormone releasing hormone (GHRH), somatostatin, oxytocin, atrial natriuretic factor (ANF), thyrotropin releasing hormone (TRH), deoxyribonuclease (DNase), prolactin, follicle stimulating hormone (FSH), and analogues thereof.

65. The method of claim 50, wherein the polypeptide is of molecular weight (MW) up to about 15 kD.

66. The method of claim 50, wherein the melezitose is present in an amount of between 20% and almost 100% by weight of the powder.

67. The method of claim 50, wherein at least 80% of the polypeptide in the formulation is in the form of (a) primary particles having a diameter of between 0.01 and 10 microns, or (b) agglomerates of said particles.

68. The method of claim 50, wherein the melezitose consists essentially of particles having a diameter of less than about 10 microns.

69. The method of claim 50, wherein the melezitose consists essentially of particles of diameter over 20 microns.

70. The powder formulation of claim 1, said powder formulation being suspended in a propellant suitable for aerosol delivery.

71. The method of claim 48, comprising the additional step of adjusting the pH of the solution prior to removing the solvent.

72. The method of claim 48, comprising the additional step of micronising the solid to produce a micronised powder.

* * * * *